United States Patent [19]

Tillander

[11] 4,066,084

[45] Jan. 3, 1978

[54] BLOOD EMPTYING DEVICE

[76] Inventor: Hans Tillander, Humlegardsgatan 3, S-412 74 Goteborg, Sweden

[21] Appl. No.: 689,347

[22] Filed: May 24, 1976

Related U.S. Application Data

[63] Continuation-in-part of Ser. No. 540,431, Jan. 13, 1975, abandoned.

[30] Foreign Application Priority Data

Jan. 14, 1974 Sweden .............................. 7400412

[51] Int. Cl.² ............................................ A61B 17/12
[52] U.S. Cl. .................................. 128/327; 128/24 R
[58] Field of Search ........ 128/327, DIG. 5, DIG. 20, 128/24 R, 38–40, 64, 60, 303 R

[56] References Cited

U.S. PATENT DOCUMENTS

| 2,044,691 | 6/1936 | Hoflinger | 128/327 |
| 2,781,041 | 2/1957 | Weinberg | 128/24 R |
| 3,454,010 | 7/1969 | Lilligren et al. | 128/327 |

Primary Examiner—Lawrence W. Trapp
Attorney, Agent, or Firm—Brumbaugh, Graves, Donohue & Raymond

[57] ABSTRACT

A blood emptying device presses the blood from an extremity towards the heart of a patient prior to a surgical incision. The device comprises a number of sections arranged around the extremity which are to be filled with a gaseous medium, a valve between a first and a second section for allowing the first section to fill to a predetermined pressure before the second section is filled, the first section retaining the predetermined pressure as the second is filled, and an operation device for operating the valve to empty the sections.

6 Claims, 5 Drawing Figures

BLOOD EMPTYING DEVICE

This application is a continuation-in-part of abandoned copending U.S. patent application Ser. No. 540,431, filed Jan. 13, 1975 and relates to a blood emptying device to be used for emptying the extremities of blood prior to a surgical incision.

The object of the present invention is to obtain a blood emptying device by means of which a simple blood emptying of an extremity may take place without using big physical force and without risk for obtaining further damages.

It is previously known at surgical incisions on extremities, as well as at restorative incisions of other kinds, to empty the extremity of blood and by means of a cuff or tube having been pumped up with air, to prevent the blood from streaming back into the extremity. An incision during such conditions is said to be an incision in a blood-emptied area.

The blood emptying procedure has heretofore taken place in such a way that one by means of an elastic rubber roller, a so called Esmarck's roller, has wrapped the extremity hard from the periphery towards the body and in such a way prevented the arterial blood from driving out into the extremity. Each revolution of the roller shall cover the previous one to one third of the extremity and the roller shall be stretched between each revolution. This is hard and troublesome work especially when the bones of the extremity are broken and the work needs great care and habit in order not to develop damages.

When the extremity has been wrapped so that only a decimeter is left of the proximal part a special kind of cuff is applied, which is pumped up with air to a pressure which is well above the blood pressure of the patient. The roller can then be removed, whereby the cuff prevents the blood from streaming back into the extremity.

This troublesome and some times damage developing method can now surprisingly be eliminated by using the present invention, which is characterized in that the valves are arranged to allow a gaseous medium to pass from one section to an other when a predetermined gas pressure has been obtained in a first section, the first section of the device being connected to an operating device via a filling tube, which operating device in one position is arranged to allow the gaseous medium to pass to the valves and into the sections and in a second position is arranged to open the valves for emptying the sections.

According to one suitable embodiment of the invention an operation tube is arranged to the operation device for controlling the opening and the closing, respectively, of the valves.

According to another embodiment of the invention the valves comprise a spring-biassed ball-valve, the opening-pressure of which is arranged to be varied by means of a regulating device.

According to a further suitable embodiment of the invention the valves are provided with a pressure piston which by means of a pressure medium introduced into the operation tube is arranged to raise the ball-valve for emptying of the sections.

According to another suitable embodiment of the invention the valves are provided with a pressure piston which by means of a pressure medium introduced into the operation tube is arranged to keep the ball-valve in closed position, whereby at the removal of the pressure medium the ball-valve opens for emptying of the sections.

The present invention will be described in the following with reference to the attached drawings wherein.

Figures 1, 2:
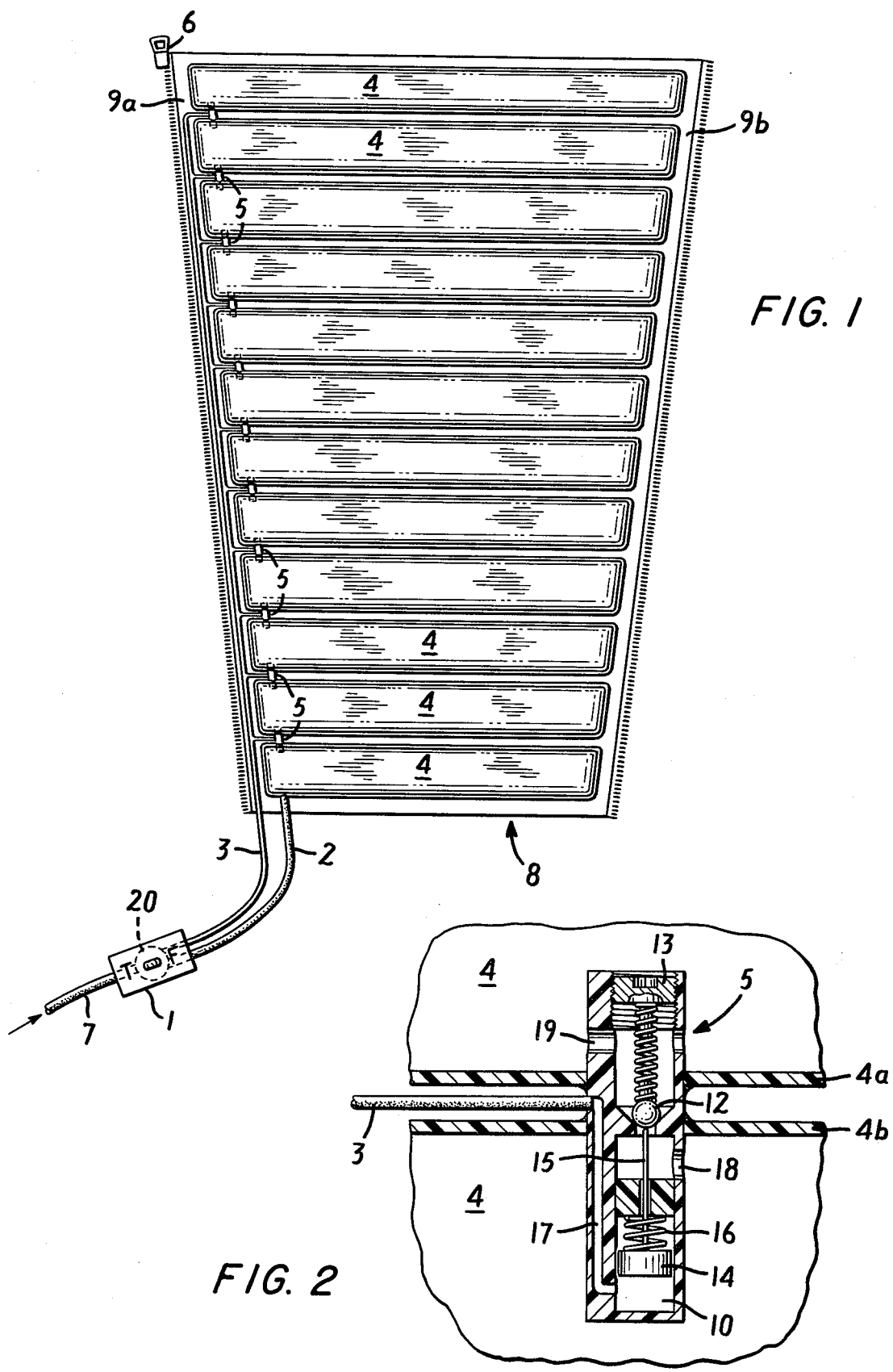
FIG. 1 shows one suitable preferred embodiment of the blood emptying device according to the invention.
FIG. 2 shows valve construction of one suitable embodiment of said blood device according to FIG. 1.

An operation device 1 is connected to a cuff 8 comprising a piece of stable fabric or plastic material of soft but not elastic quality by means of a filling tube 2 and an operation tube 3. The main shape of the cuff is that of an isosceles triangle being truncated, i.e. it has the shape of a parallel trapezium, the two non-parallel sides having the same length. The two non-parallel sides 9a and 9b of the cuff 8 are provided with a divisible zip fastener 6, by means of which the cuff can be shaped to a slightly cone shaped cylinder.

On one side of the form stable material a number of sections 4 are provided, which sections are longish and are arranged parallel to the parallel sides of the parallel trapezium. The sections 4 are manufactured of an elastic, strong plastic material, rubber or other air impervious material. The sections may also consist of balloons attached to a pocket in the cuff.

The sections 4 are further connected in series by means of special valves 5 connecting said sections, which valves are arranged to open first when a certain pressure has been obtained on its pressure side.

To the cuff 8 belongs also the above mentioned operation device 1. The operation device contains a reducing valve and a reversal valve 20. The reducing valve reduces an inlet air pressure from a tube 7 to 350 mm Hg. From the operation device leads the filling tube 2 and the operation tube 3, the former being relatively coarse and the latter being of a relatively fine caliber.

The valves 5 consist of a ball valve, where the ball 12 can be pressed against its seat by means of an adjusting force adjustable by an adjusting screw 13. The walls of the sections 4 are, in FIG. 2, marked with 4a and 4b whereby air can pass from the lower section, in the figure, via an opening 18 and the ball-valve to the upper section, in the figure, through an opening 19, as soon as the air pressure exceeds the pressure by means of which the ball 12 presses against its seat.

The valve 5 is further provided with a certain operation cylinder 10 in which a piston 14 can move and with a pin 15 raise the ball from its seat regardless of the air pressure in the sections. A return spring 16 is also arranged to remove the piston 14 to its original position. In the operation cylinder 10 a channel 17 ends which channel is connected to the operation tube 3 of the operation device 1.

When the blood emptying cuff 8 is to be used it is placed under the extremity to be emptied and is closed around it by means of the zip fastener 6. The reversal valve 20 of the operation device 1 is put on T (according to the figure) whereby air can pass the reducing valve and the filling tube 2 to the first section, which thereby is filled with air. When the pressure in this section has reached the preadjusted value of the ball-valve, suitably 300 mm Hg the ball 12 raises and air streams to the next section. The air fills, in this way, section after section until the whole cuff has been filled with air. The blood has now been driven in a central direction, i.e. in direction towards the heart. An ordinary pressure cuff is then arranged around the extremity above the blood emptying cuff and is pumped up to a suitable pressure.

The reversal valve of the operation device is now put on F (according to the figure), whereby the filling tube 2 is connected with the outer air at the same time as the pressure air with the pressure of 350 mm Hg is guided to the operation tube 3 and via this to all the valves 5.

Via the channels 17 and the pressure pistons 14 the balls are now raised from their seats and air can stream from the upper sections to the lower sections and out via the filling tube 2. The blood emptying cuff is then removed whereupon the operation can start.

During the whole blood emptying procedure the extremity has been in absolute quiet and the work has been done by the cuff, whereby troublesome physical work and not the least the risk for complications has been eliminated.

Figure 4:
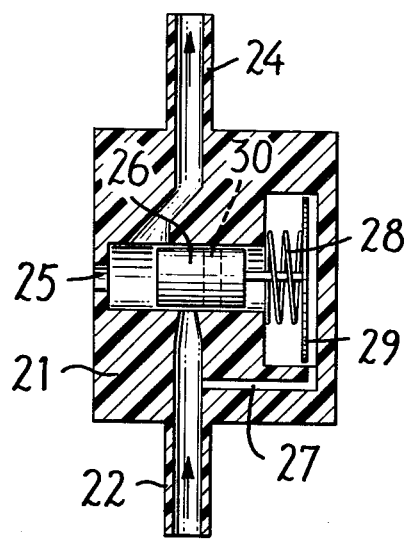
FIG. 4 is a side view, partly in cross section, of still another embodiment.
Figure 5:
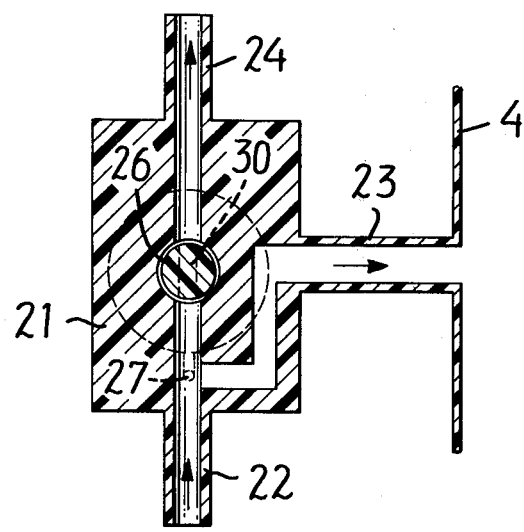
FIG. 5 is a front view, in cross section, of the embodiment shown in FIG. 4.

It has been shown above that the valves 5 connect the sections 4 by being placed in the intermediate walls of the sections, with one opening in each section; and in such a way connecting the sections. The sections can also be connected by means of tubes in which tubes the valves 5 are arranged. As shown in FIGS. 4 and 5, such valves may comprise an inlet opening 22 connected to the tube from a preceding section, an outlet opening 23 to the section inflated through the valve, and an outlet opening 24 to the tube leading to the next valve. The inlet opening 22 is also connected via passage 27 to a piston 29 which is connected to a valve member 26 and urged by a spring 28 to a position in which the valve member blocks the inlet opening 22 from the outlet opening 24. When the pressure in the section inflated through valve reaches a predetermined valve at which it overcomes the spring force, the piston moves the valve member to connect the inlet to the outlet through passage 30 in the valve member for inflating the next section. When the pressure in the preceding section is released by operation of the operating device, the spring moves the piston and valve member back to the position shown in FIG. 4 to connect the next section (via outlet 24) to opening 25 for releasing the pressure.

Figure 3:
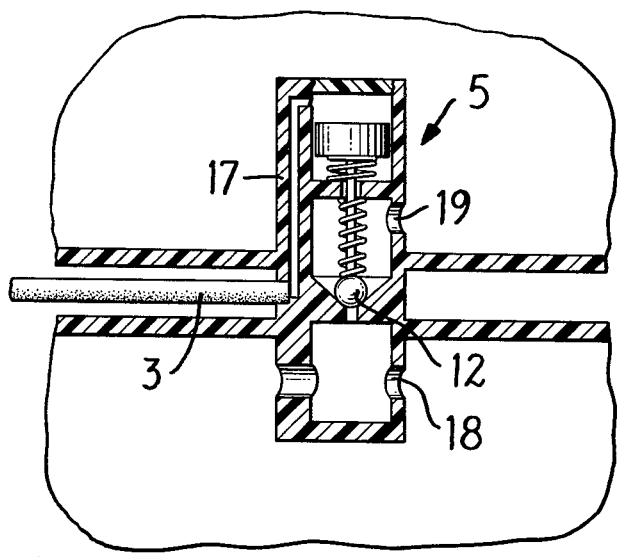
FIG. 3 is a view, partly in cross section, of another embodiment.

The valves 5 have been described above to open in response to pressure for emptying of the sections 4. The valves may, however, also be construed for operation by release of a pressure to empty the sections directly through each valve (see FIG. 3).

I claim:

1. Blood collecting device intended to be used in the emptying of extremities of blood before a surgical incision and comprising a number of sections (4) connected in series to receive and retain a gaseous medium, a number of valves (5) connecting said sections in said series comprising pressure-responsive means for allowing a gaseous medium to pass from one section to another only when a predetermined gas pressure has been obtained in a next preceding section and retaining the predetermined pressure in each filled section as the other sections are filled, a filling tube (2) connecting a first section of the device to an operating device (1), and the operating device which in one position is arranged to allow the gaseous medium to pass to the valves (5) and into the sections (4) and in a second position is arranged to open the valves (5) for emptying the sections.

2. A device according to claim 1, wherein an operation tube (3) additionally connects the operation device (1) to each valve (5) for controlling the opening and the closing, respectively, of the valves (5) in dependence upon the position of the operating device.

3. A device according to claim 2 wherein the valves (5) comprise a spring-biassed ball-valve (12), the opening-pressure of which is arranged to be varied by means of a regulating device (13).

4. A device according to claim 3, wherein the valves (5) are provided with pressure piston (14) which by means of a pressure medium introduced into the operation tube (3) is arranged to raise the ball-valve (12) for emptying of the sections (4).

5. A device according to claim 3 wherein the valves (5) are provided with a pressure piston, which, by means of a pressure medium introduced into the operation tube (3), is arranged to keep the ball-valve (12) in a closed position, whereby at the removal of the pressure medium the valve (12) opens for emptying of the sections (4).

6. A device according to claim 1, wherein the valves are arranged in a filling tube outside the respective sections (4), the valves comprising an inlet opening communicating with the filling tube, an outlet opening to one sections (4), an outlet opening to the next valve, means for opening the outlet opening to the next valve when the predetermined pressure has been obtained in the one section, and an outlet opening comprising means for letting the gaseous medium from one section out when operation pressure is applied from the operating device.

* * * * *